US012784886B2

(12) United States Patent
Soltani Bidgoli et al.

(10) Patent No.: US 12,784,886 B2
(45) Date of Patent: Nov. 3, 2026

(54) METHOD AND SYSTEM OF USING HIERARCHICAL VECTORISATION FOR REPRESENTATION OF HEALTHCARE DATA

(71) Applicant: KNOWTIONS RESEARCH INC., Toronto (CA)

(72) Inventors: Rohollah Soltani Bidgoli, Toronto (CA); Alexandre Tomberg, Toronto (CA); Anthony Lee, Toronto (CA)

(73) Assignee: KNOWTIONS RESEARCH INC., Toronto (CA)

( * ) Notice: Subject to any disclaimer, the term of this patent is extended or adjusted under 35 U.S.C. 154(b) by 821 days.

(21) Appl. No.: 17/811,682

(22) PCT Filed: Jan. 12, 2021

(86) PCT No.: PCT/CA2021/050023
§ 371 (c)(1),
(2) Date: Jul. 11, 2022

(87) PCT Pub. No.: WO2021/142534
PCT Pub. Date: Jul. 22, 2021

(65) Prior Publication Data

US 2023/0178199 A1 Jun. 8, 2023

Related U.S. Application Data

(60) Provisional application No. 62/960,246, filed on Jan. 13, 2020.

(51) Int. Cl.
*G06N 20/00* (2019.01)
*G06N 3/0442* (2023.01)
(Continued)

(52) U.S. Cl.
CPC ........... *G16H 15/00* (2018.01); *G06N 3/0442* (2023.01); *G06N 3/09* (2023.01); *G06N 20/00* (2019.01); *G16H 10/60* (2018.01)

(58) Field of Classification Search
None
See application file for complete search history.

(56) References Cited

U.S. PATENT DOCUMENTS 10,705,796 B1 * 7/2020 Doyle .................. G06F 16/282
2016/0179945 A1 * 6/2016 Lastra Diaz .......... G06F 16/284 707/739

(Continued)

FOREIGN PATENT DOCUMENTS

CN 110059185 A 7/2019
TW 201705079 A 2/2017

OTHER PUBLICATIONS

Choi et al. (Choi) "GRAM: Graph-based Attention Model for Healthcare Representation Learning" KDD'17, KDD 2017 Research Paper, Aug. 13-17, 2017, Halifax, NS, Canada, DOI: http://dx.doi.org/10.1145/3097983.3098126 (Year: 2017).*

(Continued)

*Primary Examiner* — Xuyang Xia
(74) *Attorney, Agent, or Firm* — Marc Lampert; Bhole IP Law

(57) ABSTRACT

There are provided systems and methods for using a hierarchical vectoriser for representation of healthcare data. One such method includes: receiving the healthcare data; mapping the code type to a taxonomy and generating node embeddings using relationships in the taxonomy for each code type with a graph embedding model; generating an event embedding for each event including aggregating vectors associated with each parameter vector using a nonlinear mapping to the node embeddings, the event embedding including the node embeddings related to said event; generating a patient embedding for each patient by encoding including the event embeddings related to said patient; and outputting the embedding for each patient.

16 Claims, 8 Drawing Sheets

(51) Int. Cl.

| | |
|---|---|
| ***G06N 3/09*** | (2023.01) |
| ***G16H 10/60*** | (2018.01) |
| ***G16H 15/00*** | (2018.01) |

(56) References Cited

U.S. PATENT DOCUMENTS

| | | | | |
|---|---|---|---|---|
| 2017/0193185 | A1* | 7/2017 | Barker | G06F 16/334 |
| 2018/0046764 | A1* | 2/2018 | Katwala | G16H 15/00 |
| 2018/0322391 | A1* | 11/2018 | Wu | G06N 3/09 |
| 2019/0258721 | A1* | 8/2019 | Guo | G06F 16/24578 |
| 2020/0303072 | A1* | 9/2020 | Drokin | G16H 10/60 |
| 2022/0027709 | A1* | 1/2022 | Honkala | G06T 5/60 |

OTHER PUBLICATIONS

Billings "Generation and Utilization of Latent Spaces for Prediction and Interpretation", University of Cambridge, Department of Computer Science and Technology Aug. 30, 2018, researchgate.net (Year: 2018).*

International Search Report for International Application No. PCT/CA2021/050023; dated Mar. 23, 2021.

Ma, Fenglong, Yaqing Wang, Houping Xiao, Ye Yuan, Radha Chitta, Jing Zhou and Jing Gao. "Incorporating medical code descriptions for diagnosis prediction in healthcare." BMC Medical Informatics and Decision Making 19 (2019).

Qureshi, Syed Arbaaz, Sriparna Saha, Mohammed Hasanuzzaman, G. Dias and E. Cambria. "Multitask Representation Learning for Multimodal Estimation of Depression Level." IEEE Intelligent Systems 34 (2019): 45-52.

Written Opinion of the International Searching Authority for International Application No. PCT/CA2021/050023; dated Mar. 23, 2021.

Xiang et al. "Graph embedding on biomedical networks: methods, applications and evaluations". Advance Access Publication: Oct. 4, 2019. Bioinformatics, 36(4), 2020, pp. 1241-1251.

Xiaomin et al. Research Article "Predicting biomedical relationships using the know ledge and graph embedding cascade model". Jun. 13, 2019. [online].

Choi E. et al."Gram: Graph-based Attention Model for Healthcare Representation Learning". In: KDD'17, Aug. 13-17, 2017, Halifax, NS, Canada. 2017 ACM. 978-I-4503-4887—Apr. 17, 2008 pp. 787-795.

Brief Notice of the Examination from the Taiwan Intellectual Property Office for Application No. 110101202, dated Feb. 21, 2022.

* cited by examiner

METHOD AND SYSTEM OF USING HIERARCHICAL VECTORISATION FOR REPRESENTATION OF HEALTHCARE DATA

FIELD OF THE INVENTION

The following relates generally to prediction models, and more specifically to a method and system of using hierarchical vectorisation for representation of healthcare data.

BACKGROUND OF THE INVENTION

The following includes information that may be useful in understanding the present disclosure. It is not an admission that any of the information provided herein is prior art nor material to the presently described or claimed inventions, nor that any publication or document that is specifically or implicitly referenced is prior art.

Electronic health and medical record (EHR/EMR) systems are steadily gaining in popularity. Ever more facets of healthcare are recorded and coded in such systems, including patient demographics, disease history and progression, laboratory test results, clinical procedures and medications, genetics, among many others. This trove of information is a unique opportunity to learn patterns to predict various future aspects of healthcare. However, the sheer number of various coding systems used to encode this clinical information is a major challenge for anyone trying to analyze structured EHR data. Even the most widely used coding systems have multiple versions to cater to different regions of the world. Analyzing one version of the coding system may not be used for another version, let alone a different coding system. In addition to public coding systems, a multitude of private coding mechanisms that have no mappings to any public coding systems are sometimes used by insurance companies and certain hospitals. This massive variance creates problems for training systems for prediction, especially when the training data includes datasets from different systems and data sources.

SUMMARY OF THE INVENTION

In an aspect, there is provided a computer-implemented method for using a hierarchical vectoriser for representation of healthcare data, the healthcare data comprising healthcare-related code types, healthcare-related events and healthcare-related patients, the events having event parameters associated therewith, the method comprising: receiving the healthcare data; mapping the code type to a taxonomy, and generating node embeddings using relationships in the taxonomy for each code type with a graph embedding model; generating an event embedding for each event, comprising aggregating vectors associated with each parameter vector using a non-linear mapping to the node embeddings; generating a patient embedding for each patient by encoding the event embeddings related to said patient; and outputting the embedding for each patient.

In a particular case of the method, each of the node embeddings are aggregated into a respective vector.

In another case of the method, aggregating the vectors comprises an addition of summations over each event for each of the node embeddings multiplied by a weight.

In yet another case of the method, aggregating the vectors comprises self-attention layers to determine feature importance.

In yet another case of the method, the non-linear mapping comprises using a trained machine learning model, the machine learning model taking as input a set of node embeddings previously labelled with event and patient information.

In yet another case of the method, the patient embedding is determined using a trained machine learning encoder.

In yet another case of the method, the trained machine learning encoder comprises a long short-term memory artificial recurrent neural network.

In yet another case of the method, the trained machine learning encoder comprises a transformer model comprising self-attention layers.

In yet another case of the method, the method further comprising predicting future healthcare aspects associated with the patient using multi-task learning, the multi-task learning trained using a set of labels for each patient embedding according to recorded true outcomes.

In yet another case of the method, the multi-task learning comprises determining loss aggregation by defining a loss function for each of the predictions and optimizing the loss functions jointly.

In yet another case of the method, the multi-task learning comprises reweighing the loss functions according to an uncertainty for each prediction, the reweighing comprising learning a noise parameter integrated in each of the loss functions.

In another aspect, there is provided a system for using a hierarchical vectoriser for representation of healthcare data, the healthcare data comprising healthcare-related code types, healthcare-related events, and healthcare-related patients, the events having event parameters associated therewith, the system comprising one or more processors and memory, the memory storing the healthcare data, the one or more processors in communication with the memory and configured to execute: an input module to receive the healthcare data; a code module to map the code type to a taxonomy, and generate node embeddings using relationships in the taxonomy for each code type with a graph embedding model; an event module to generate an event embedding for each event, comprising aggregating vectors associated with each parameter vector using a non-linear mapping to the node embeddings; a patient module to generate a patient embedding for each patient by encoding the event embeddings related to said patient; and an output module to output the embedding for each patient.

In a particular case of the system, each of the node embeddings are aggregated into a respective vector.

In another case of the system, aggregating vectors comprises an addition of summations over each event for each of the node embeddings multiplied by a weight.

In yet another case of the system, aggregating the vectors comprises self-attention layers to determine feature importance.

In yet another case of the system, the non-linear mapping comprises using a trained machine learning model, the machine learning model taking as input a set of node embeddings previously labelled with event and patient information.

In yet another case of the system, the patient embedding is determined using a trained machine learning encoder.

In yet another case of the system, the trained machine learning encoder comprises a long short-term memory artificial recurrent neural network.

In yet another case of the system, the trained machine learning encoder comprises a transformer model comprising self-attention layers.

In yet another case of the system, the one or more processors are further configured to execute a prediction module to predict future healthcare aspects associated with the patient using multi-task learning, the multi-task learning trained using a set of labels for each patient embedding according to recorded true outcomes.

In yet another case of the system, the multi-task learning comprises determining loss aggregation by defining a loss function for each of the predictions and optimizing the loss functions jointly.

In yet another case of the system, the multi-task learning comprises reweighing the loss functions according to an uncertainty for each prediction, the reweighing comprising learning a noise parameter integrated in each of the loss functions.

For purposes of summarizing the invention, certain aspects, advantages, and novel features of the invention have been described herein. It is to be understood that not necessarily all such advantages may be achieved in accordance with any one particular embodiment of the invention. Thus, the invention may be embodied or carried out in a manner that achieves or optimizes one advantage or group of advantages as taught herein without necessarily achieving other advantages as may be taught or suggested herein. The features of the invention which are believed to be novel are particularly pointed out and distinctly claimed in the concluding portion of the specification. These and other features, aspects, and advantages of the present invention will become better understood with reference to the following drawings and detailed description.

Other aspects and features according to the present application will become apparent to those ordinarily skilled in the art upon review of the following description of embodiments of the invention in conjunction with the accompanying figures.

BRIEF DESCRIPTION OF THE DRAWINGS

Reference will now be made to the accompanying drawings which show, by way of example only, embodiments of the invention, and how they may be carried into effect, and in which.

Like reference numerals indicate like or corresponding elements in the drawings.

DETAILED DESCRIPTION OF THE EMBODIMENTS

Figure 1:
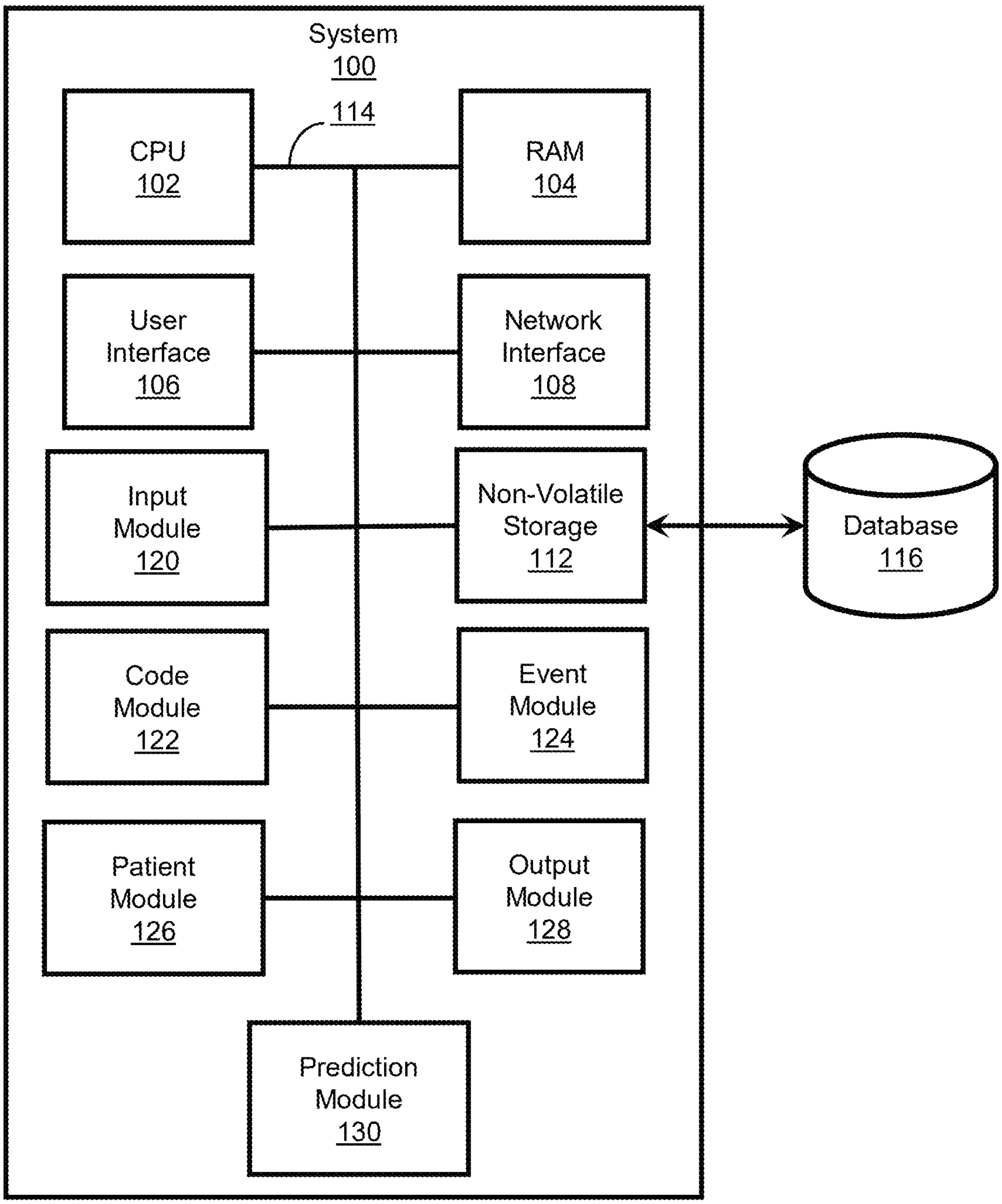
FIG. 1 is a schematic diagram of a system of using hierarchical vectorisation for representation of healthcare data, according to an embodiment.

Embodiments will now be described with reference to the figures. For simplicity and clarity of illustration, where considered appropriate, reference numerals may be repeated among the Figures to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Also, the description is not to be considered as limiting the scope of the embodiments described herein.

Various terms used throughout the present description may be read and understood as follows, unless the context indicates otherwise: "or" as used throughout is inclusive, as though written "and/or"; singular articles and pronouns as used throughout include their plural forms, and vice versa; similarly, gendered pronouns include their counterpart pronouns so that pronouns should not be understood as limiting anything described herein to use, implementation, performance, etc. by a single gender; "exemplary" should be understood as "illustrative" or "exemplifying" and not necessarily as "preferred" over other embodiments. Further definitions for terms may be set out herein; these may apply to prior and subsequent instances of those terms, as will be understood from a reading of the present description.

Any module, unit, component, server, computer, terminal, engine or device exemplified herein that executes instructions may include or otherwise have access to computer readable media such as storage media, computer storage media, or data storage devices (removable and/or non-removable) such as, for example, magnetic disks, optical disks, or tape. Computer storage media may include volatile and non-volatile, removable and non-removable media implemented in any method or technology for storage of information, such as computer readable instructions, data structures, program modules, or other data. Examples of computer storage media include RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by an application, module, or both. Any such computer storage media may be part of the device or accessible or connectable thereto. Further, unless the context clearly indicates otherwise, any processor or controller set out herein may be implemented as a singular processor or as a plurality of processors. The plurality of processors may be arrayed or distributed, and any processing function referred to herein may be carried out by one or by a plurality of processors, even though a single processor may be exemplified. Any method, application or module herein described may be implemented using computer readable/executable instructions that may be stored or otherwise held by such computer readable media and executed by the one or more processors.

The following relates generally to prediction models, and more specifically to computer-based method and system of using hierarchical vectorisation for representation of healthcare data.

Referring now to FIG. 1, a system of using hierarchical vectorisation for representation of healthcare data, in accordance with an embodiment, is shown. In this embodiment, the system 100 is run on a local computing device (26 in FIG. 2). In further embodiments, the local computing device 26 can have access to content located on a server (32 in FIG.

Figure 2:
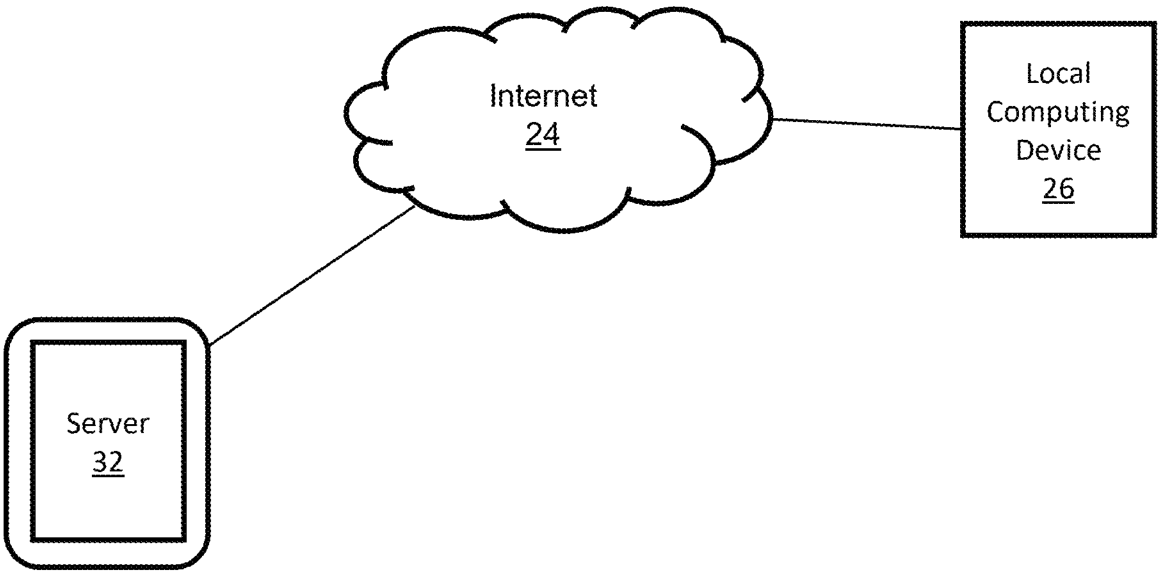
FIG. 2 is a schematic diagram showing the system of FIG. 1 and an exemplary operating environment.

2) over a network, such as the internet (24 in FIG. 2). In further embodiments, the system 100 can be run on any suitable computing device; for example, the server (32 in FIG. 2).

In some embodiments, the components of the system 100 are stored by and executed on a single computer system. In other embodiments, the components of the system 100 are distributed among two or more computer systems that may be locally or remotely distributed.

FIG. 1 shows various physical and logical components of an embodiment of the system 100. As shown, the system 100 has a number of physical and logical components, including a central processing unit ("CPU") 102 (comprising one or more processors), random access memory ("RAM") 104, a user interface 106, a network interface 108, non-volatile storage 112, and a local bus 114 enabling CPU 102 to communicate with the other components. In some cases, at least some of the one or more processors can be graphical processing units. CPU 102 executes an operating system, and various modules, as described below in greater detail. RAM 104 provides relatively responsive volatile storage to CPU 102. The user interface 106 enables an administrator or user to provide input via an input device, for example a keyboard and mouse. The user interface 106 can also output information to output devices to the user, such as a display and/or speakers. The network interface 108 permits communication with other systems, such as other computing devices and servers remotely located from the system 100, such as for a typical cloud-based access model. Non-volatile storage 112 stores the operating system and programs, including computer-executable instructions for implementing the operating system and modules, as well as any data used by these services. Additional stored data can be stored in a database 116. During operation of the system 100, the operating system, the modules, and the related data may be retrieved from the non-volatile storage 112 and placed in RAM 104 to facilitate execution.

In an embodiment, the system 100 further includes a number of functional modules that can be executed on the CPU 102; for example, an input module 120, a code module 122, an event module 124, a patient module 126, an output module 128, and a prediction module 130. In some cases, the functions and/or operations of the modules can be combined or executed on other modules.

In the healthcare space, data can be accumulated from a number of sources, such as collected from hospital records and insurance company files. However, each data source or data holder may host their respective data in different formats (in some cases, in proprietary formats). Accordingly, it is a substantial technical challenge to map the various data such that it can be imported in a way that provides a means for analyzing such data. For example, by measuring a distance in an embedding space from one patient to another. Analysis of the data can be used for any number of applications; for example, determining patient analytics, medical event detection, or recognizing fraud. With respect the fraud example, measuring the distance of one patient to numerous others can be used to determine similarity, which can be used to detect fraud.

Embodiments of the present disclosure can generate a feature vector for data from varied healthcare data sources using hierarchical vectorisation. In some cases, hierarchical vectorisation can be used to encode groupings to code-level representations; for example, diagnoses, procedures, medications, tests, claims, and the like. The embodiments can encode each of these code-level representations to a visit vector, and each visit vector to a patient vector. This patient vector, encompassing the hierarchical encodings, can be used for various applications; for example, as input to a machine learning model to make healthcare related predictions. In this way, embodiments of the present disclosure can use the hierarchical vectoriser (also referred to as "H.Vec") as a multi-task prediction model to provide multilayer representation of healthcare-related events.

Advantageously, patient embeddings used in the present embodiments do not require use of a time window. This is advantageous because it allows the system to look at a patient's full history.

To advantageously leverage the ability of deep learning models to learn complex features from input data, input healthcare data can be transformed into multilevel vectors. In an example, the healthcare data can include electronic health records (EHR) data and/or medical insurance claims data. In some embodiments, each patient can be represented as a sequence of visits; with each visit can be represented as a multilevel structure with inter-code relationships. In an example, the codes can include demographics, diagnoses, procedures, medications, lab tests, notes and reports, claim codes, and the like.

Figure 3:
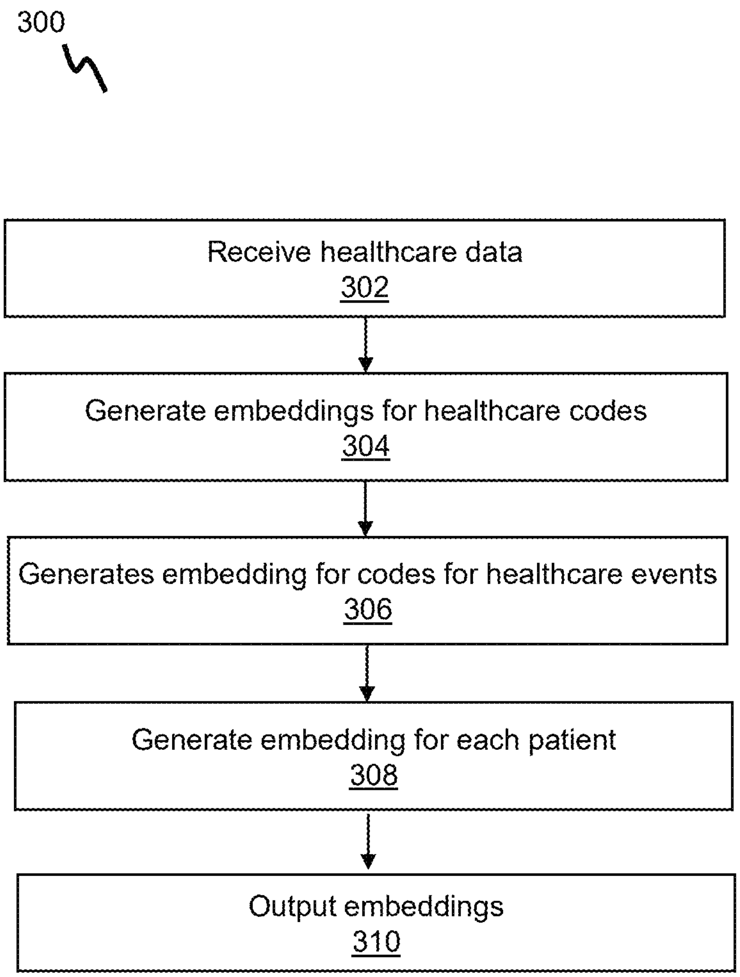
FIG. 3 is a flowchart of a method of using hierarchical vectorisation for representation of healthcare data, according to an embodiment.

Turning to FIG. 3, a flowchart for a method 300 of using hierarchical vectorisation for representation of healthcare data, according to an embodiment, is shown.

At block 302, an input module 120 receives the healthcare data; for example, via the database 116, the network interface 108 and/or the user interface 106.

At block 304, the code module 122 generates node embeddings for healthcare codes, for example, medical codes, drug codes, services codes, and the like. Generating the node embeddings comprises mapping the code type to a taxonomy and generating node embeddings using relationships in the taxonomy for each code type using a graph embedding model. Generally, for each healthcare code, there can be a unique node embedding to represent that code. Healthcare coding can have hundreds of thousands of distinct codes that represent all aspects of healthcare. Some medical codes, for example those for rare diseases, may appear infrequently in EHR datasets. Thus, training a robust prediction model with these rare codes is a substantial technical challenge. In view of this challenge, the code module 122 trains a low-dimensional embedding of the healthcare codes. The low-dimensional embedding is a vector with a smaller dimension than a vector comprising all the codes; in some cases, a significantly smaller dimension. In most cases, the vector distance between two embeddings corresponds, at least approximately, to a measure of similarity between corresponding codes and their respective healthcare concepts. In an example, each healthcare concept can be mapped to a respective representation generated based on relations in a SNOMED™ taxonomy. In this way, the embedding can represent the taxonomy position and the structure of the neighborhood in the taxonomy; and thus, can be generated using context, location and neighborhood nodes in the knowledge graph. In this way, medical concepts, represented by healthcare codes, that are related to each other and thus have similar embeddings, can be closer to each other in low dimensional space. In some cases, to construct taxonomy embeddings, a node-to-vector (node2vec) approach can be used as the graph embedding model.

At block 306, the event module 124 generates an embedding for codes related to a healthcare event into a multilevel structure with inter-code relationships. Healthcare events, such as clinical events and patient visits, are usually represented by sets of medical codes because healthcare practitioners often use multiple codes for a particular event; for example, to describe a patient's diagnosis or prescribe a list of medications to that same patient. Each event is embedded by the event module 124 as a multilevel structure with inter-code relationships; for example, containing a varying number of demographics, diagnoses, procedures, medications, lab tests, notes and reports, and claim codes. In an example embodiment, six categories of embeddings can be used:

- Demographics vector: comprises the patient's demographic information at the time of the healthcare event; for example, their age, gender, marital status, location, and occupation. In some cases, categorical variables (for example, gender, marital status, and profession) can be represented by a one-hot representation vector. Feature vectors representing each of the patient's demographic information can be concatenated to make the demographics vector for each event.
- Diagnosis vector: comprises aggregated embeddings of diagnosis codes related to the healthcare event.
- Procedure vector: comprises aggregated embeddings of procedure codes related to the healthcare event.
- Medication vector: comprises aggregated embeddings of prescription codes related to the healthcare event.
- Lab test vector: comprises aggregated embeddings of laboratory test codes related to the healthcare event.
- Claim items vector: comprises categorical variables related to the healthcare event. Such categorical variables can include, for example, hospital department, case type, institution, various claimed amounts (for example, diagnoses claimed amounts and medication claimed amounts), and the like. In some cases, categorical variables can be represented by a one-hot representation vector and all amounts can be log transformed.

In further embodiments, only some of the above categories of embeddings can be used, or further categories can be added, as appropriate. As the healthcare codes are mapped to an embedding, for example of size 128, using the categorization, for example into the above six groups, can be used to have different sets of weight and patterns applied to them.

At block 308, the patient module 126 generates a single embedding for each patient. The patient module 126 can consider the entire healthcare event history of a patient as a sequence of episodes of care. Each episode can consist of multiple events; for example, multiple hospital visits and hospitalizations. Each event has associated parameters; for example, diagnosis, treatments, and tests. The parameter vectors are aggregated (for example, aggregating the diagnosis, treatment and test vectors) to produce an event embedding. Multiple event embeddings are aggregated, for example, in a way that preserves the sequential nature of healthcare events to generate a patient's healthcare history embedding.

At block 310, the output module 128 outputs one or more of the patient embedding, the event embeddings, and the healthcare code embeddings. In some cases, the one or more embeddings can be used as input to predict an aspect of healthcare, as described herein.

Accordingly, event embeddings can be the result of applying the non-linear multilayer mapping function on top of the categories of representation. The patient embedding can be the result of applying a sequential and/or time-series model (for example, long short term memory network (LSTM)) on top of the sequence of event embedding of each patient. The present disclosure describes using LSTM, which has been experimentally verified by the present inventors as providing substantial accurate results; however, in further cases, any model can be used that can capture sequential pattern in data, for example, recurrent neural network (RNN), gated recurrent units (GRUs), one dimensional convolutional neural network (CNN), self attention based models (for example, transformer based models) and the like. Training and testing of the model can be based on multi-task training of the H.Vec, which, in some cases, can involve simultaneously training the model to learn the readmission, mortality, costs, length of stay, and the like.

Figure 4:
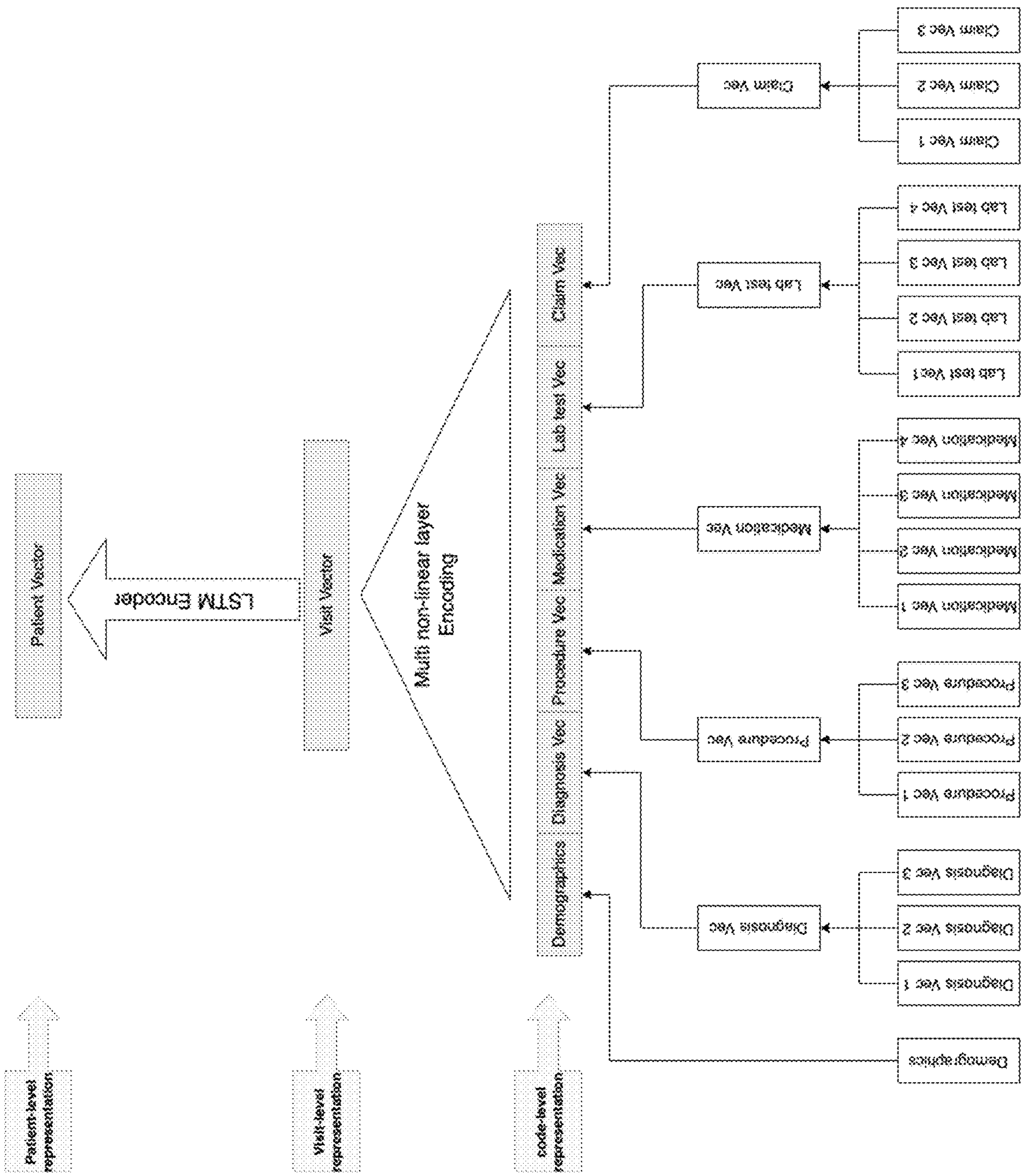
FIG. 4 illustrates an example conceptual structure for an embodiment of the system of FIG. 1.

FIG. 4 illustrates an example conceptual structure for an embodiment of the system 100. In this example, hypothetical patient P has a sequence of visits (as the healthcare events) $V_1, V_2, V_3, \ldots V_t$ over time. Each visit $V_t$ contains demographic information as a demographic vector $S_t$, a set of diagnosis embeddings $D_{t1}, D_{t2}, D_{t3}, \ldots D_{tn}$ aggregated into a diagnosis vector, a set of procedure embeddings $P_{t1}, P_{t2}, P_{t3}, \ldots P_{tn}$ aggregated into a procedure vector, a set of medication embeddings $M_{t1}, M_{t2}, M_{t3}, \ldots M_{tn}$ aggregated into a medication vector, a set of lab test embeddings $L_{t1}, L_{t2}, L_{t3}, \ldots L_{tn}$ aggregated into a lab test vector, and a set of claim embeddings $C_{t1}, C_{t2}, C_{t3}, \ldots C_{tn}$ aggregated into a claim vector. Any suitable linear or non-linear mapping function can be used for aggregation; for example, a summation function, a one dimensional convolutional neural network (CNN), and a self attention based model (for example, transformer based models). The patient embedding can be determined as an encoding of the visit vectors as follows:

$$P=f(V_1,V_2,V_3, \ldots V_t)$$

where $f$, in this example, is an LSTM model. In further cases, any suitable machine learning encoder can be used, for example other types of artificial neural networks such as feedforward neural networks or other types of recurrent neural networks.

In this way, the visit representation at time t can be determined as follows:

$$V_t = g\left(W_s S_t + W_d \sum_{i=1}^{n} D_{ti} + W_P \sum_{i=1}^{n} P_{ti} + W_m \sum_{i=1}^{n} M_{ti} + W_l \sum_{i=1}^{n} L_{ti} + W_c \sum_{i=1}^{n} C_{ti}\right)$$

where g is is a non-linear mapping function that maps the data, and Wis the weight corresponding to each aggregated (in this case, summed) vector. The non-linear mapping function in this case can be multiple layers of the artificial neural network with a non-linear activation function; for example, tang or rectified linear unit (ReLU). In some cases, the weightings of the artificial neural network can be initially set to random values.

Figure 5:
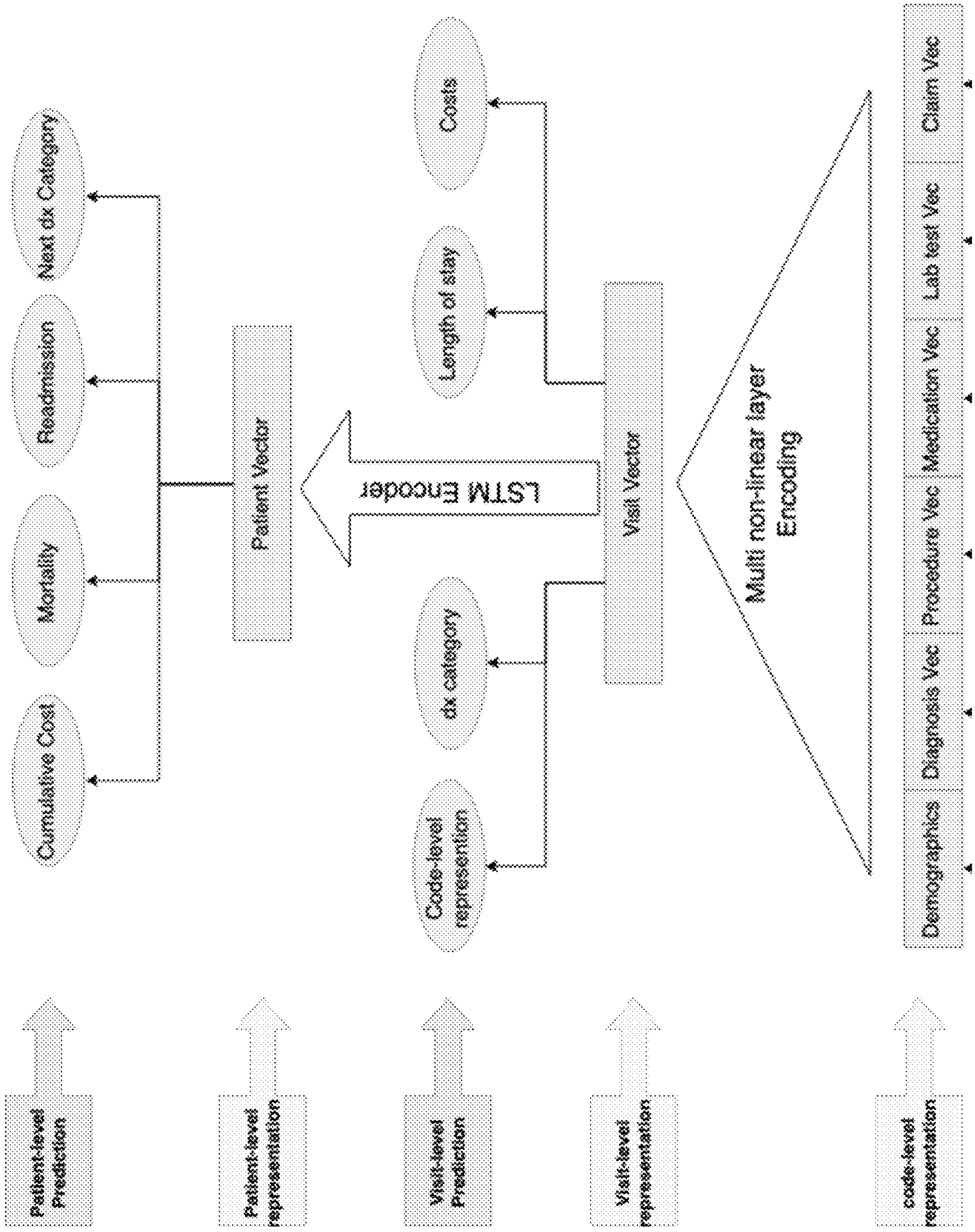
FIG. 5 illustrates an example conceptual structure for healthcare aspect prediction using the embodiment of the system of FIG. 1.

In an embodiment, the prediction module 130 can use a multi-task learning (MTL) approach to predict a future healthcare aspect of the patient based on the embeddings generated in method 300. By having multiple auxiliary tasks, and by sharing representations between related tasks, the prediction module 130 can be used to generate better generalizations using MTL. A conceptual structure for an example of such prediction is illustrated in FIG. 5. In the example of FIG. 5, the prediction module 130 predicts the aspects of future cumulative costs, mortality, readmission, and next diagnosis (dx) category. In further cases, other aspects can be predicted. In some cases, the prediction can be predicted using the patient level embedding; for example, readmission, mortality, future cost, future procedure, future admission rate, and the like. In some cases, the tasks can be derived from the data itself, referred to as self supervised learning; for example, readmission, mortality, autoencoder, or created through additional labeling. In some cases, the prediction task can be a classification task; for example, a binary classification task like predicting readmission, or a regression task, like predicting cost or length of stay.

Such an approach can inductively transfer knowledge contained in multiple auxiliary prediction tasks to improve a deep learning model's generalization performance on a prediction task. The auxiliary task can help the model to produce better and more generalizable results for the main task. The auxiliary tasks can also force the model to capture information from the claim and pass it through the event/visit and patient level embeddings of the model. This can allow the model to be able to better predict those tasks; thus, generating more informative and generalizable embeddings for events and patients. MTL can help the deep learning model focus its attention on features that matter because other tasks can provide additional evidence for the relevance or irrelevance of such features. In some cases, as a kind of additional regularization, such features can boost the performance of the main prediction task. The present inventors conducted example experiments showing that MTL improves model robustness in healthcare concept embedding. In some cases, the auxiliary prediction tasks can be a classification task; for example, a binary classification task like predicting readmission, or a regression task like predicting cost or length of stay.

In some cases, to predict outcomes, a set of labels can be predicted for each patient embedding according to recorded true outcomes. These are called the auxiliary prediction tasks. In some cases, auxiliary prediction tasks can be chosen such that they are easy to be learned and use labels that can be obtained with low effort. In the example of FIG. 5, the auxiliary prediction tasks could be predicting a code-level representation, a diagnosis (dx) category, a length of stay, and cost of visit. In another example, three examples of auxiliary prediction tasks could be:

- Length of stay prediction: The duration of hospitalization is determined, and a label is generated for each patient. Labels of patients in the training set can be used in training, and labels for patients in validation and test sets can be used to calibrate the model and to evaluate the prediction.
- Diagnosis (dx) category prediction: The category of all the diagnosis of a visit is predicted for each patient.
- Readmission prediction: The risk of readmission within 30 days is predicted after discharging from the hospital for each patient.

The prediction module 130 can perform MTL loss aggregation by defining a loss function for the auxiliary prediction tasks and optimize the loss functions jointly. For example, by adding the losses and optimizing this joint loss. In an embodiment, the MTL can include multi-task learning using uncertainty. In this embodiment, the losses can be reweighed according to each task's uncertainty. This can be accomplished by learning another noise parameter that is integrated in the loss function for each task. This allows having multiple tasks, for example regression and classification, and bringing all losses to the same scale. In this way, the prediction module 130 can learn multiple tasks with different scales simultaneously. For regression tasks, the model likelihood can be defined as a Gaussian with mean given by the model output:

$$P(y \mid f(x)) = \mathcal{N}(f(x), \sigma 2)$$

For classification tasks, the likelihood of the model can be a scaled version of the model output through a softmax function:

$$P(y \mid f(x), \sigma) = Softmax(1/\sigma 2 * f(x))$$

with an observation noise scalar σ.

In another embodiment, the MTL can include adapting auxiliary losses using gradient similarity. In this embodiment, the cosine similarity between gradients of tasks can be used as an adaptive weight to detect when an auxiliary loss is helpful to a main loss. Whenever there is a main prediction task, the other auxiliary prediction task losses can be used where they are sufficiently aligned with the main task.

The code module 122 can generate the node embeddings for healthcare codes using any suitable embedding approach; for example, word vector models such as GloVe and FastText.

Figure 6:
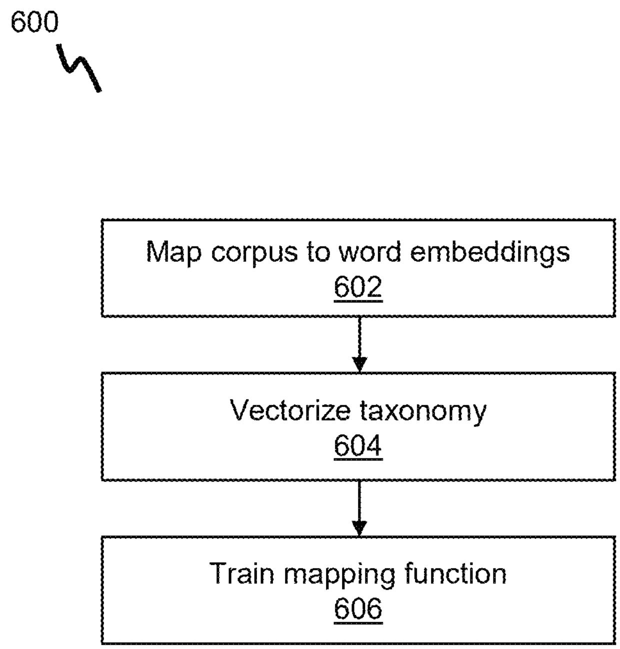
FIG. 6 is a flowchart of an approach for mapping text values to a taxonomy.
Figure 7:
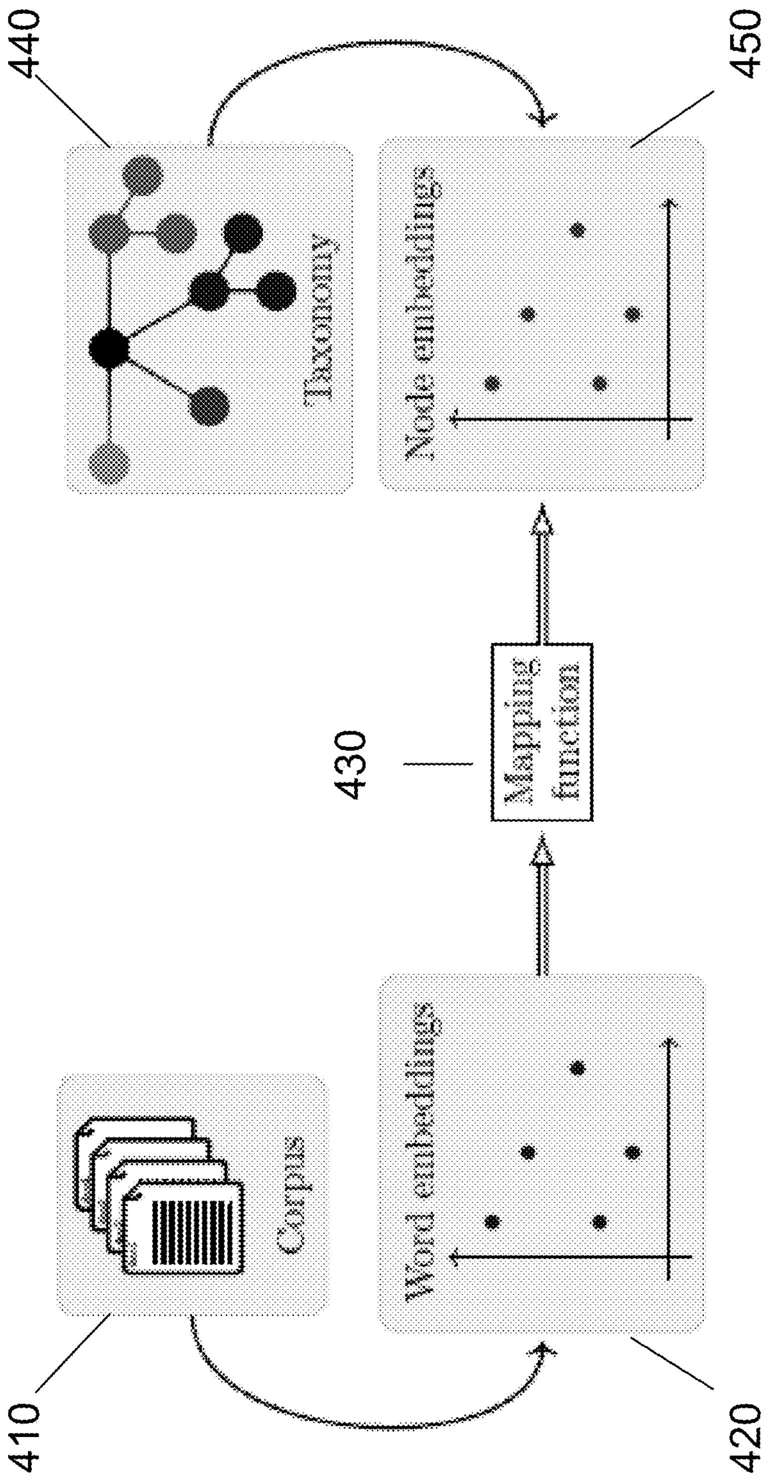
FIG. 7 is an example of a mapping function for the approach of FIG. 6.

In another example approach, the code module 122 can generate the node embeddings for healthcare codes by incorporating taxonomical medical knowledge. A flowchart of this approach is shown in FIGS. 6 and 7. There are three main stages: first, the lexicon or corpus 410 is mapped 602 to word embeddings 420; second, the taxonomy 430 is vectorized 604 using node embeddings 440; and finally, the mapping function 450 is trained 606 to connect the two embedding spaces. Word embeddings 420, when, for example, trained on a biomedical corpus may capture the semantic meaning of medical concepts better than embeddings trained on an unspecialized set of documents. Thus, open access papers may be used to construct the corpus 410 (source for example from PubMed), free text admission and discharge notes (source for example from MIMICIII Clinical Database), narratives (source for example from the US Food and Drug Administration (FDA) Adverse Event Reporting System (FAERS), and a part of the 2010 Relations Challenge from i2b2). The documents from those sources may be pre-processed to split sentences, add spaces around punctuation marks, change all characters to lowercase, and reformat to one sentence per line. Finally, all files may be concatenated into a single document. In an example using the above-mentioned sources, the single document comprises 235M sentences and 6.25B words to create the corpus 410. The corpus 410 may then be used to train the algorithms for mapping the word embeddings 420.

In the above example, learning word embeddings can be accomplished using, for example, GloVe and FastText. An important distinction between them is the treatment of words that are not part of the training vocabulary: GloVe creates a special out-of-vocabulary token and maps all of these words to this token's vector, while FastText uses subword information to generate an appropriate embedding. In an example, vector space dimensionality can be set to 200 and the minimal number of word occurrences to 10 for both algorithms; producing a vocabulary of 3.6 million tokens.

The taxonomy 430 to which the mapping module 124 maps phrases can use any suitable taxonomy 430 to which the mapping module 124 maps phrases. For the biomedical example described herein, a 2018 international version of SNOMED CT may be used as the target graph G=(V, E). In this example, the vertex set V consists of 392 thousand medical concepts and the edge set E is composed of 1.9 million relations between the vertices; including is_a relationships and attributes such as finding_site and due_to.

To construct taxonomy embeddings, any suitable embedding approach can be used. In an example, the node2vec approach can be used. In this example approach, a random walk may start on the edges from each vertex $v \in V$ and stop after a fixed number of steps (20 in the present example). All the vertices visited by the walk may be considered part of the graph neighbourhood N(v) of v. Following a skip-gram architecture, in this example, a feature vector assignment function $v \mapsto f_{n2v}(v) \in \mathbb{R}^{128}$ may be selected by solving an optimization problem:

$$f_{n2v} = \underset{f}{\operatorname{argmax}} \sum_{u \in V} \log \mathbb{P}[N(u) | f(u)]$$

using, for example, stochastic gradient descent and negative sampling.

The mapping between phrases and concepts in the target taxonomy may be generated by associating points in the node embedding vector space to sequences of word embeddings corresponding to individual words in a phrase. The input phrase can be split into words that are converted to word embeddings and fed into the mapping function, with the output of the function being a point in the node embedding space (in the above example, $\mathbb{R}^{128}$). Thus, given a phrase consisting of n words with the associated word embeddings $w_1, \ldots, w_n$, the mapping function is m: $(w_1, \ldots, w_n) \mapsto p$, where p is a point in the node embedding vector space (in the above example, $p \in \mathbb{R}^{128}$). In some cases, to complete the mapping, concepts in the taxonomy whose node embeddings are the closest to the point p are used. In an example experiment of the biomedical example, the present inventors tested two measures of closeness in the node embedding vector space $\mathbb{R}^{128}$: Euclidean $\ell_2$ distance and cosine similarity; that is $$\ell_2 \text{ distance } (p, q) = \|p - q\| - \sqrt{(p-q)\cdot(p-q)},$$

$$\text{cos similarity } (p, q) = \frac{p \cdot q}{\|p\|\|q\|}.$$

In some cases, for example to compute the top-k accuracy of the mapping, a list of k closest concepts may be used.

The exact form of the mapping function m may vary. Three different architectures are provided as examples herein, although others may be used: a linear mapping, a convolutional neural network (CNN), and a bidirectional long short term memory network (Bi-LSTM). In some cases, phrases can be padded or truncated. For example, in the above example, padded or truncated to be exactly 20 words long to represent each phrase by 20 word embeddings $w_1, \ldots w_{20} \in R^{200}$ in order to accommodate all three architectures.

For linear mapping, a linear relationship can be derived between the word embeddings and the node embeddings. In the above example, 20 word embeddings may be concatenated into a single 4000 dimensional vector w, and the linear mapping given by p=m(w)=Mw for a 4000×128 matrix M.

For the CNN, convolutional filters of different sizes can be applied to the input vectors. The feature maps produced by the filters can then be fed into a pooling layer followed by a projection layer to obtain an output of desired dimension. In an example, filters representing word windows of sizes 1, 2, 3, and 5 may be used, followed by a maximum pooling layer and a projection layer to 128 output dimensions. CNN is a nonlinear transformation that can be advantageously used to capture complex patterns in the input. Another advantageous property of the CNN is an ability to learn invariant features regardless of their position in the phrase.

Bi-LSTM is also a non-linear transformation. For the Bi-LSTM, this type of neural network can be used to operate by recursively applying a computation to every element of the input sequence conditioned on the previous computed results in both forward and backward directions. Bi-LSTM may be used for learning long distance dependencies in its input. In the above example, a Bi-LSTM can be used to approximate the mapping function m by building a single Bi-LSTM cell with 200 hidden units followed by a projection layer to 128 output dimensions.

In a specific example, training data was gathered consisting of phrase-concept pairs from the taxonomy itself. As nodes in SNOMED™ CT may have multiple phrases describing them (synonyms), each synonym-concept pair was considered separately for a total of 269K training examples. To find the best mapping function m* in each of the three architectures described above, the supervised regression problem $$m_* = \underset{m}{\operatorname{argmin}} \sum_{(phrase,node)} \|m(\text{phrase}) - f_{n2v}(\text{node})\|_{\ell_2}^2$$

can be solved using, for example, an Adam optimizer for 50 epochs.

In further embodiments, self-attention layers, in attention based models, can be used for the non-linear mapping, described herein. Self-attention layers are a non-linear transformation that is a type of artificial neural network used to determine feature importance. Self-attention operates by receiving three input vectors: Q, K, and V, referred to as query, key and value, respectively. Each of the inputs is of size n. The self-attention layer generally comprises five steps:

1. Multiply the query (Q) vector and the key (K) vector;
2. Scale the result of step #1 by a factor T;
3. Divide the result of step #2 by the square root of the size of the input vectors (n);
4. Apply a softmax function to the result of step #3; and
5. Multiply the result of step #4 by the value (V) vector.

The result will be a vector of size n, that has one of the features increased (generally considered important) and the other features are decreased (generally considered not important). Self-attention layers determine importance via:

$$\text{Attention}(Q, K, V) = \text{softmax}\left(\frac{QK^T}{\sqrt{n}}\right)V$$

A self-attention layer learns through many training data examples about which features are important. In an embodiment, the attention layers are applied on the node embeddings and applied on the event embeddings. In some cases, a multi-headed self-attention layer can be used; that uses multiple attention nodes in parallel, which allows the self attention layer to place importance on multiple features.

Figure 8:
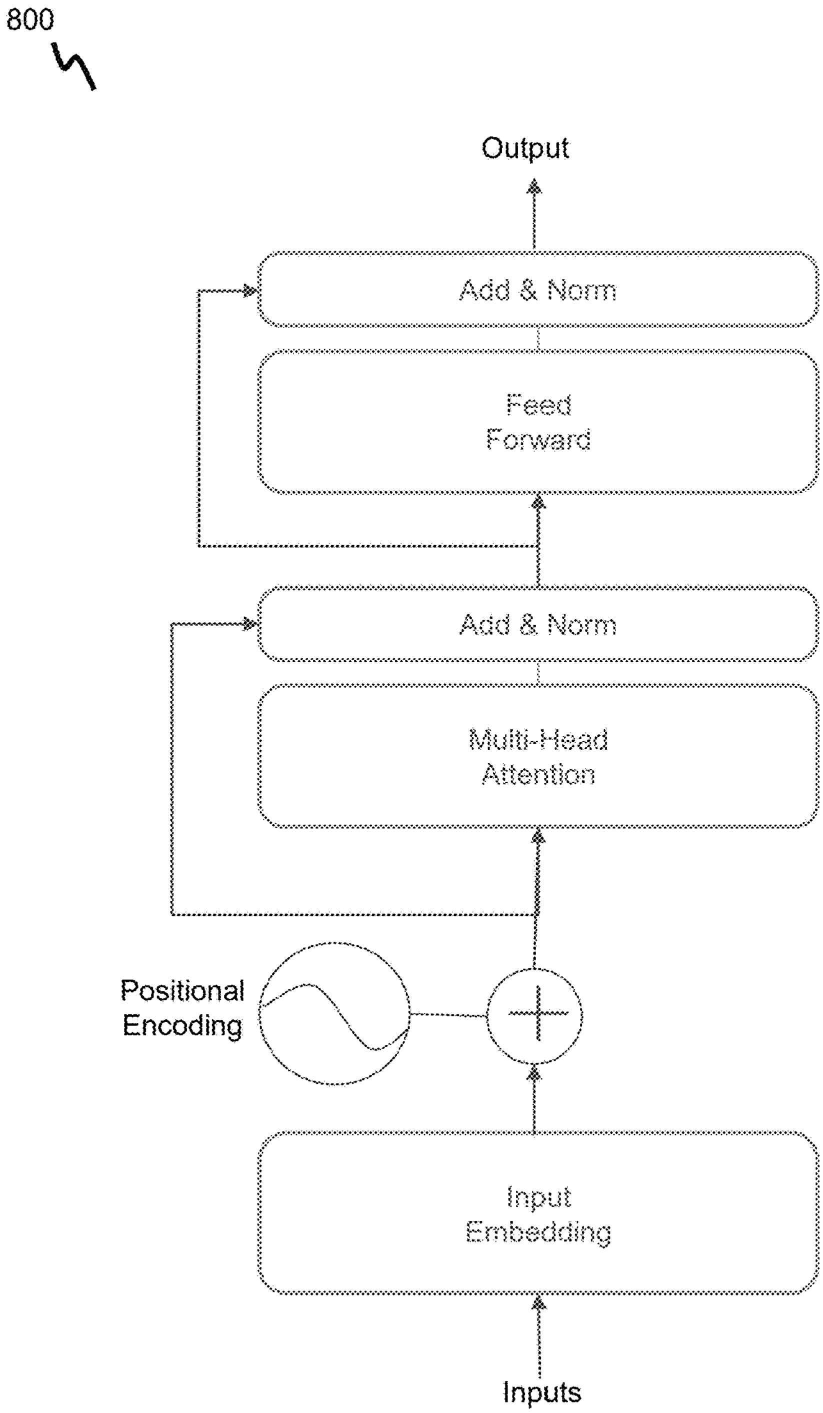
FIG. 8 illustrates an example of an architecture of a transformer model.

In some embodiments, a transformer model 800 can be used as an attention based model, as illustrated in the example of FIG. 8. FIG. 8 illustrates inputs being fed into an input embedding and combined with positional encoding. The output of this combination is fed into multi-head attention layers, then added and normalized. The output of this addition and normalization is fed into a feed-forward network, which is then added and normalized and outputted. In some cases, the transformer model 800 can be considered a single layer of a multi-layer transformer model, each layer performed in series or parallel. The transformer model uses self-attention to draw global dependencies between input and output to determine representations of its input. The transformer model can be applied without having to use sequence-aligned RNNs or convolution. Transformer architectures can advantageously learn longer-term dependency and avoid the use of a time window. In each step, it advantageously applies a self-attention mechanism which directly models relationships between all features in input, regardless of their respective position.

The present invention may be embodied in other specific forms without departing from the spirit or essential characteristics thereof. Certain adaptations and modifications of the invention will be obvious to those skilled in the art. Therefore, the presently discussed embodiments are considered to be illustrative and not restrictive, the scope of the invention being indicated by the appended claims rather than the foregoing description and all changes which come within the meaning and range of equivalency of the claims are therefore intended to be embraced therein. Additionally, the entire disclosures of all references cited above are incorporated herein by reference.

The invention claimed is:

1. A computer-implemented method of using a hierarchical vectoriser pipeline for representation of healthcare data, the healthcare data comprising a plurality of different healthcare-related code types, the healthcare data further comprising healthcare-related events and healthcare-related patients, the healthcare-related events having event parameters for a respective healthcare-related code type associated therewith, the method comprising:

receiving the healthcare data;

at a first level of the hierarchical vectoriser pipeline, mapping each of the plurality of different healthcare-related code types to a taxonomy using a measure of closeness of a health-related concept represented by the respective healthcare-related code type to points in a mapping, and generating node embeddings using relationships in the taxonomy for each code type of the plurality of different healthcare-related code types with a graph embedding model, wherein a vector distance between two respective node embeddings corresponds to a measure of similarity between corresponding code types and their respective healthcare-related concepts;

at a second level of the hierarchical vectoriser pipeline, generating an event embedding for each event comprising aggregating vectors to the node embeddings using a non-linear mapping that comprises an artificial neural network, each vector associated with a parameter vector of the respective healthcare-related code type;

at a third level of the hierarchical vectoriser pipeline, generating a patient embedding for each patient by encoding, using a machine learning encoder, a sequence of the event embeddings related to said patient; and outputting the patient embedding for each patient for use by a multi-task machine learning model to predict a future healthcare-related aspect of the patient using the patient embedding as input, wherein the multi-task learning comprises determining loss aggregation by defining a loss function for each of predictions and optimizing loss functions jointly and reweighing the loss functions according to an uncertainty for each prediction, the reweighing comprising learning a noise parameter integrated in each of the loss functions to bring all losses to the same scale.

2. The method of claim 1, wherein each of the node embeddings are aggregated into a respective vector.

3. The method of claim 2, wherein aggregating the vectors comprises an addition of summations over each event for each of the node embeddings multiplied by a weight.

4. The method of claim 2, wherein aggregating the vectors comprises self-attention layers to determine feature importance.

5. The method of claim 1, wherein the trained artificial neural network takes as input a set of node embeddings previously labelled with event and patient information.

6. The method of claim 1, wherein the trained machine learning encoder comprises a long short-term memory artificial recurrent neural network.

7. The method of claim 1, wherein the trained machine learning encoder comprises a transformer model comprising self-attention layers.

8. The method of claim 1, further comprising predicting future healthcare aspects associated with the patient using multi-task learning, the multi-task learning trained using a set of labels for each patient embedding according to recorded true outcomes.

9. A system for using a hierarchical vectoriser pipeline of representation of healthcare data, the healthcare data comprising a plurality of different healthcare-related code types, the healthcare data further comprising healthcare-related events and healthcare-related patients, the healthcare-related events having event parameters for a respective healthcare-related code type associated therewith, the system comprising one or more processors and memory, the memory storing the healthcare data, the one or more processors in communication with the memory and configured to:

receive the healthcare data;

at a first level of the hierarchical vectoriser pipeline, map each of the plurality of different healthcare-related code types to a taxonomy using a measure of closeness of a health-related concept represented by the respective healthcare-related code type to points in a mapping, and to generate node embeddings using relationships in the taxonomy for each code type of the plurality of different healthcare-related code types with a graph embedding model, wherein a vector distance between two respective node embeddings corresponds to a measure of similarity between corresponding code types and their respective healthcare-related concepts; at a second level of the hierarchical vectoriser pipeline, generate an event embedding for each event comprising aggregating vectors to the node embeddings using a non-linear mapping that comprises an artificial neural network, each vector associated with a parameter vector of the respective healthcare-related code type;

at a third level of the hierarchical vectoriser pipeline, generate a patient embedding for each patient by encoding, using a machine learning encoder, a sequence of the event embeddings related to said patient; and output the patient embedding for each patient for use by a multi-task machine learning model to predict a future healthcare-related aspect of the patient using the patient embedding as input, wherein the multi-task learning comprises determining loss aggregation by defining a loss function for each of predictions and optimizing loss functions jointly and reweighing the loss functions according to an uncertainty for each prediction, the reweighing comprising learning a noise parameter integrated in each of the loss functions to bring all losses to the same scale.

10. The system of claim 9, wherein each of the node embeddings are aggregated into a respective vector.

11. The system of claim 10, wherein aggregating vectors comprises an addition of summations over each event for each of the node embeddings multiplied by a weight.

12. The system of claim 11, wherein aggregating the vectors comprises self-attention layers to determine feature importance.

13. The system of claim 9, wherein the trained artificial neural network takes as input a set of node embeddings previously labelled with event and patient information.

14. The system of claim 9, wherein the trained machine learning encoder comprises a long short-term memory artificial recurrent neural network.

15. The system of claim 9, wherein the trained machine learning encoder comprises a transformer model comprising self-attention layers.

16. The system of claim 9, wherein the one or more processors are further configured to execute a prediction module to predict future healthcare aspects associated with the patient using multi-task learning, the multi-task learning trained using a set of labels for each patient embedding according to recorded true outcomes.

* * * * *